(12) United States Patent
Vaxman et al.

(10) Patent No.: US 10,249,092 B2
(45) Date of Patent: Apr. 2, 2019

(54) SYSTEM AND METHOD FOR RENDERING COMPLEX DATA IN A VIRTUAL REALITY OR AUGMENTED REALITY ENVIRONMENT

(71) Applicant: SIMBIONIX LTD., Airport City (IL)

(72) Inventors: Yaron Vaxman, Petach Tikva (IL); Niv Fisher, Ramat Gan (IL); Roy Porat, Tel Aviv (IL); Oren Kalisman, Tel Aviv (IL)

(73) Assignee: SIMBIONIX LTD., Airport City (IL)

( * ) Notice: Subject to any disclaimer, the term of this patent is extended or adjusted under 35 U.S.C. 154(b) by 0 days.

(21) Appl. No.: 15/360,330

(22) Filed: Nov. 23, 2016

(65) Prior Publication Data

US 2018/0144550 A1 May 24, 2018

(51) Int. Cl.
*G06T 19/00* (2011.01)
*G06T 17/00* (2006.01)
*G06T 17/20* (2006.01)
*G06T 19/20* (2011.01)

(52) U.S. Cl.
CPC ............ *G06T 19/006* (2013.01); *G06T 17/20* (2013.01); *G06T 19/20* (2013.01); *G06T 2219/2012* (2013.01)

(58) Field of Classification Search
CPC ............................... G06T 19/006; G06T 17/20
USPC ......................................................... 345/424
See application file for complete search history.

(56) References Cited

U.S. PATENT DOCUMENTS

| 6,084,979 A | 7/2000 | Kanade et al. | |
|---|---|---|---|
| 2009/0177454 A1 | 7/2009 | Bronstein et al. | |
| 2010/0016658 A1 | 1/2010 | Zou et al. | |
| 2012/0230566 A1 | 9/2012 | Dean et al. | |
| 2013/0009948 A1* | 1/2013 | Berger | G06T 19/00 345/419 |
| 2015/0138201 A1 | 5/2015 | Brown | |
| 2015/0359430 A1 | 12/2015 | Ben-Haim | |
| 2016/0026253 A1 | 1/2016 | Bradski et al. | |
| 2016/0071316 A1* | 3/2016 | Beeler | G06T 17/20 345/423 |

OTHER PUBLICATIONS

Ahmed et al. A Modified Fuzzy C-Means Algorithm for Bias Field Estimation and Segmentation of MRI Data, IEEE Transactions on Medical Imaging, vol. 21, No. 3, Mar. 2002, 193-199.
Kindlmann, Gordon Lothar, Semi-Automatic Generation of Transfer Functions for Direct Volume Rendering, A Thesis Presented to the Faculty of the Graduate School of Cornell University in Partial Fulfillment of the Requirements for the Degree of Master of Science, Jan. 1999, 1-155.

* cited by examiner

*Primary Examiner* — Hai Tao Sun
(74) *Attorney, Agent, or Firm* — Pearl Cohen Zedek Latzer Baratz LLP

(57) ABSTRACT

Methods for virtual reality and augmented reality rendering of a 3D object are provided. The methods can include segmenting the 3D object such that portions of the 3D object can be identifiable and distinguishable. The methods can include creating masks, identifying relationships between the masks and marking the masks accordingly.

14 Claims, 3 Drawing Sheets

SYSTEM AND METHOD FOR RENDERING COMPLEX DATA IN A VIRTUAL REALITY OR AUGMENTED REALITY ENVIRONMENT

FIELD OF THE INVENTION

The present invention relates generally to rendering imaging data to a format that can be viewed in virtual reality or augmented reality. More specifically, the present invention relates to rendering three-dimensional (3D) objects in virtual reality or augmented reality.

BACKGROUND OF THE INVENTION

Current virtual reality or augmented reality systems exist and generally include displaying computer-generated simulations of 3D objects on one or more two-dimensional (2D) screens. Creating a 2D image based on a 3D object can require substantial computing resources. Known systems and methods typically suffer from poor performance. For example, since many samples (of a 3D object) and calculations can be required to determine values of pixels in a 2D frame, some known systems and methods may not provide an adequate resolution. Additionally, when operations such as zoom or rotate are required, known systems and methods suffer from a delay.

In addition, visualizing 3D objects having one or more parts that have topologies that are overlapping (e.g., are tangent to each other) can be a complicated task, especially in virtual reality ("VR") and/or augmented reality ("AR"). For example, the 3D objects are typically displayed using meshes. Meshes that are created based on 3D objects that have overlapping parts (e.g., mutual topology) typically result in the overlapping parts being indistinguishable from each other. For example, when tangent and separate 3D objects have meshes with mutual topology, then current systems typically create meshes that intersect. However, meshes of tangent and separate 3D objects typically should not intersect, because for example, it typically does not allow for an accurate representation of the fact that the 3D objects are separate.

Due to, for example, the stereo vision in AR/VR technologies, the intersecting meshes can be detectably by a user. Known systems and methods can fail to adequately create a mesh (or a set of meshes) from different 3D objects that can be accurate for visualization in AR/VR technologies.

SUMMARY OF THE INVENTION

One advantage of the invention is that it can provide AR/VR visualization of complex anatomies (e.g., anatomy having overlapping objects) in a manner that allows a viewer to distinguish between the objects. Another advantage of the invention is that it can provide a clearer understanding to a user of the 3D object, due to, for example an accurate representation of the 3D object.

Accordingly, in an aspect of the invention, a method and a non-transient computer readable medium containing program instructions for causing a computer to perform the method for creating a three-dimensional (3D) virtual reality or augmented reality rendering of an object from imaging data.

According to embodiments of the present invention, an object type based on imaging data is determined, a set of masks based on the object type are created. Each mask can represent a unique portion of the object, and can be assigned a plurality of voxels from the imaging data that corresponds to the respective mask's unique portion and a unique visual marker.

An outer mask of the set of masks can be determined, and a 3D mesh can be created from the outer mask. For each vertex in an inner wall of the 3D mesh of the outer mask, a geodesic distance for each voxel is determined for each mask, except for the outer masks, to a respective current voxel is determined, and the respective visual marker of the current vertex can be modified to have the same visual marker as the voxel with the shortest geodesic distance to the vertex. A 3D virtual reality or augmented reality rendering of the object based on the outer mask and the respective unique visual marker of all of the masks may be created.

In some embodiments, for each voxel in the plurality of voxels that is not assigned to a mask, one mask from the set of masks having a voxel that is within a nearest distance to the current voxel may be determined, and a visual marker may be assigned to the current voxel that is the same as the unique visual marker of the one mask. The unique visual marker may be a color marker, a pattern, or any combination thereof.

In some embodiments, the outer mask may be modified by applying a box filter that has a predetermined threshold.

In certain embodiments, the determination of the outer mask may be based on user input, the object type, or any combination thereof.

BRIEF DESCRIPTION OF THE DRAWINGS

Non-limiting examples of embodiments of the disclosure are described below with reference to figures attached hereto that are listed following this paragraph. Identical features that appear in more than one figure are generally labeled with a same label in all the figures in which they appear. A label labeling an icon representing a given feature of an embodiment of the disclosure in a figure may be used to reference the given feature. Dimensions of features shown in the figures are chosen for convenience and clarity of presentation and are not necessarily shown to scale.

The subject matter regarded as the invention is particularly pointed out and distinctly claimed in the concluding portion of the specification. The invention, however, both as to organization and method of operation, together with objects, features and advantages thereof, may best be understood by reference to the following detailed description when read with the accompanied drawings. Embodiments of the invention are illustrated by way of example and not limitation in the figures of the accompanying drawings, in which like reference numerals indicate corresponding, analogous or similar elements, and in which:

Figure 1:
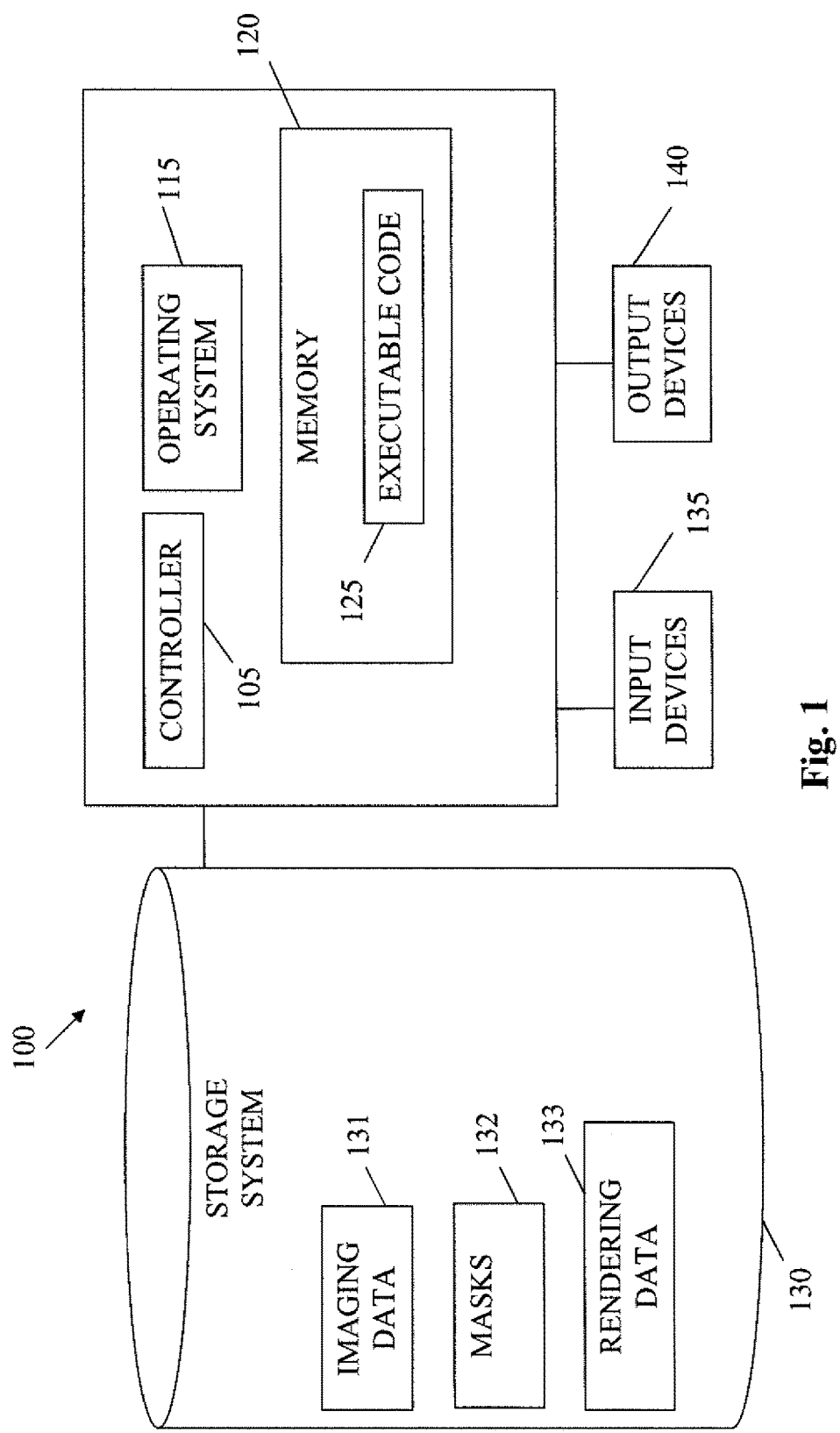
FIG. 1 shows a high-level block diagram of an exemplary computing device according to some embodiments of the present invention.

It will be appreciated that for simplicity and clarity of illustration, elements shown in the figures have not necessarily been drawn accurately or to scale. For example, the dimensions of some of the elements may be exaggerated relative to other elements for clarity, or several physical components may be included in one functional block or element. Further, where considered appropriate, reference numerals may be repeated among the figures to indicate corresponding or analogous elements.

DETAILED DESCRIPTION

In the following detailed description, numerous specific details are set forth in order to provide a thorough understanding of the invention. However, it will be understood by those skilled in the art that the present invention may be practiced without these specific details. In other instances, well-known methods, procedures, and components, modules, units and/or circuits have not been described in detail so as not to obscure the invention. Some features or elements described with respect to one embodiment may be combined with features or elements described with respect to other embodiments. For the sake of clarity, discussion of same or similar features or elements may not be repeated.

Although embodiments of the invention are not limited in this regard, discussions utilizing terms such as, for example, "processing," "computing," "calculating," "determining," "establishing", "analyzing", "checking", or the like, may refer to operation(s) and/or process(es) of a computer, a computing platform, a computing system, or other electronic computing device, that manipulates and/or transforms data represented as physical (e.g., electronic) quantities within the computer's registers and/or memories into other data similarly represented as physical quantities within the computer's registers and/or memories or other information non-transitory storage medium that may store instructions to perform operations and/or processes. Although embodiments of the invention are not limited in this regard, the terms "plurality" and "a plurality" as used herein may include, for example, "multiple" or "two or more". The terms "plurality" or "a plurality" may be used throughout the specification to describe two or more components, devices, elements, units, parameters, or the like. The term set when used herein may include one or more items. Unless explicitly stated, the method embodiments described herein are not constrained to a particular order or sequence. Additionally, some of the described method embodiments or elements thereof can occur or be performed simultaneously, at the same point in time, or concurrently.

Reference is made to FIG. 1, showing a high-level block diagram of an exemplary computing device (or system) according to some embodiments of the present invention. Computing device 100 may include a controller 105 that may be, for example, a central processing unit processor (CPU), a chip or any suitable computing or computational device, an operating system 115, a memory 120, executable code 125, a storage system 130, input devices 135 and output devices 140.

Controller 105 (or one or more controllers or processors, possibly across multiple units or devices) may be configured to carry out methods described herein, and/or to execute or act as the various modules, units, etc. More than one computing device 100 may be included in, and one or more computing devices 100 may be, or act as, the components of a system according to an illustrative embodiment of the invention. For example a first computing device 100 may carry out a method of 3D model creation and a second computing device 100 may carry out a method of rendering the model on a display.

Operating system 115 may be or may include any code segment (e.g., one similar to executable code 125 described herein) designed and/or configured to perform tasks involving coordination, scheduling, arbitration, supervising, controlling or otherwise managing operation of computing device 100, for example, scheduling execution of software programs or executable code segments, or enabling software programs or other modules or units to communicate. Operating system 115 may be a commercial operating system.

Memory 120 may be or may include, for example, a Random Access Memory (RAM), a read only memory (ROM), a Dynamic RAM (DRAM), a Synchronous DRAM (SD-RAM), a double data rate (DDR) memory chip, a Flash memory, a volatile memory, a non-volatile memory, a cache memory, a buffer, a short term memory unit, a long term memory unit, or other suitable memory units or storage units. Memory 120 may be or may include a plurality of, possibly different, memory units. Memory 120 may be a computer or processor non-transitory readable medium, or a computer non-transitory storage medium, e.g., a RAM.

Executable code 125 may be any executable code, e.g., an application, a program, a process, task or script. Executable code 125 may be executed by controller 105 possibly under control of operating system 115. For example, executable code 125 may be an application that automatically creates a 3D model and/or renders an image on a monitor as further described herein. Although, for the sake of clarity, a single item of executable code 125 is shown in FIG. 1, a system according to an illustrative embodiment of the invention may include a plurality of executable code segments similar to executable code 125 that may be loaded into memory 120 and cause controller 105 to carry out methods described herein. For example, units or modules described herein may be, or may include, controller 105, memory 120 and executable code 125.

Storage system 130 may be or may include, for example, a hard disk drive, a Compact Disk (CD) drive, a CD-Recordable (CD-R) drive, a Blu-ray disk (BD), a universal serial bus (USB) device or other suitable removable and/or fixed storage unit. Content may be stored in storage system 130 and may be loaded from storage system 130 into memory 120 where it may be processed by controller 105. As shown, storage system 130 may include a 3D object store (e.g., imaging data store 131), masks 132 and rendering data 133. Data stored in storage system 130 is further described herein.

The 3D object store can include 3D objects. The 3D object can include any data that is representative of a 3D object. The 3D objects can include 3D imaging data, mesh data, volumetric objects, polygon mesh objects, point clouds, functional representations of 3D objects, cad files, 3D pdf files, STL files, and/or any inputs that can represent a 3D object. The 3D imaging data can include medical imaging data, including Computed Tomography ("CT") imaging data, a Cone Beam Computed Tomography ("CBCT") imaging data, a Magnetic Resonance Imaging ("MRI") imaging data and/or MRA imaging data (e.g., MRI with a contrast agent) or ultrasound imaging data. The 3D objects can be of anatomy (e.g., complex anatomy), industrial data, or any 3D object.

In some embodiments, some of the components shown in FIG. 1 may be omitted. For example, memory 120 may be a non-volatile memory having the storage capacity of storage system 130. Accordingly, although shown as a separate component, storage system 130 may be embedded or included in memory 120.

Input devices 135 may be or may include a mouse, a keyboard, a touch screen or pad or any suitable input device. It will be recognized that any suitable number of input devices may be operatively connected to computing device 100 as shown by block 135. Output devices 140 may include one or more screens, displays or monitors, speakers and/or any other suitable output devices. It will be recognized that any suitable number of output devices may be operatively connected to computing device 100 as shown by block 140.

Any applicable input/output (I/O) devices may be connected to computing device 100 as shown by blocks 135 and 140. For example, a wired or wireless network interface card (NIC), a printer, a universal serial bus (USB) device or external hard drive may be included in input devices 135 and/or output devices 140.

A system according to an illustrative embodiment of the invention may include components such as, but not limited to, a plurality of central processing units (CPU) or any other suitable multi-purpose or specific processors or controllers (e.g., controllers similar to controller 105), a plurality of input units, a plurality of output units, a plurality of memory units, and a plurality of storage units. The system may additionally include other suitable hardware components and/or software components. In some embodiments, a system may include or may be, for example, a personal computer, a desktop computer, a laptop computer, a workstation, a server computer, a network device, or any other suitable computing device. For example, a system as described herein may include one or more devices such as computing device 100.

Imaging data 131 may be any imaging data as known in the art, e.g., imaging data 131 may be medical data such as produced by a computerized tomography (CT) system or by a magnetic resonance imaging (MRI) system and/or by a cone beam computed tomography (CBCT) system.

A mask included in masks 132 may be, may reference, or may be related to a set of objects in a 3D model. For example, a mask may list, or point to, a set of objects, e.g., voxels in imaging data may be associated with (or included in) a mask. A mask may be, for example, data construct including for example Boolean (e.g., I/O, yes/no) values for each voxel or data point in a larger data set. A mask may include visual markers (e.g., color and/or patterns) that specify appearance of the voxel. The mask when applied to the larger data set may indicate that a voxel is marked or is not marked. A voxel is known in the art, generally, a voxel may be an element of a group of elements of a volume, the volume may represent (e.g., using digital data as known in the art) a 3D space and/or a 3D object.

Rendering data 133 may be any data usable for rendering an image on a screen or monitor. For example, rendering data 133 may be a set of pixel values (e.g., red, green and blue (RGB) values, hue, intensity and so on) that may be used in order to render an image as known in the art.

In some embodiments of the invention, the system can receive, as input, imaging data of an object (e.g., an organ such as a head or heart). The system can store and retrieve masks from memory and/or receive a set of masks that correspond to a type of the object. The system can populate each mask in the set of masks with corresponding imaging data. For example, an imaging data of a heart, a left chamber mask and a right chamber mask can be retrieved from memory. A portion of the imaging data that corresponds to the right chamber of the heart can be assigned to the right chamber mask and the portion of the imaging data that corresponds to the left chamber mask can be assigned to the left chamber mask.

The system can render the set of masks having assigned imaging data into a format that can be viewed in virtual reality or augmented reality (e.g., a virtual reality or augmented reality rendering into a 3D model of the organ or object). Any file format may be used, for example, embodiments of the invention may use formats such as the standard triangle language (STL) or polygon file format or the stanford triangle format (PLY). For example, based on imaging data received from a CT or an MRI system and based on a set of masks, some embodiments may produce a 3D colored virtual reality or augmented reality rendering of a heart chamber, a blood vessel or system and so on.

Some embodiments may create a 3D virtual reality or augmented reality rendering of a segmented object (e.g., a cardiac area of a heart) and the virtual reality or augmented reality rendering may be used to display the segmented object in a virtual reality or augmented reality (VR) system, e.g., via VR glasses such as Oculus Rift or Microsoft's HoloLens headset.

In some embodiments the 3D virtual rendering may be colored. For example, a blood vessel in a colored virtual reality or augmented reality rendered 3D model may be red, a bone may be white and so on. A virtual reality or augmented reality rendered 3D model may include any number of colors, e.g., it may include only black and white colors, various shades of gray or any colors along the color spectrum.

As described above, the virtual reality or augmented reality rendering of imaging data can be done by assigning the imaging data to one or more masks of a set of mask. Each mask can represent a set of voxels. Some embodiments may perform various operations (e.g., morphological operations) on (or involving) masks by manipulating voxels included in, or listed, represented or referenced by, the masks.

For example, a group A of voxels may be dilated with spherical element of radius R (denoted herein as "A⊕R"), a group A of voxels may be eroded with spherical element of radius R (denoted herein as "A⊖R"), a group A of voxels may be opened with spherical element of radius R (denoted herein as "A⊙R") and a group A of voxels may be closed with spherical element of radius R (denoted herein as "A⊙R").

Figure 2A:
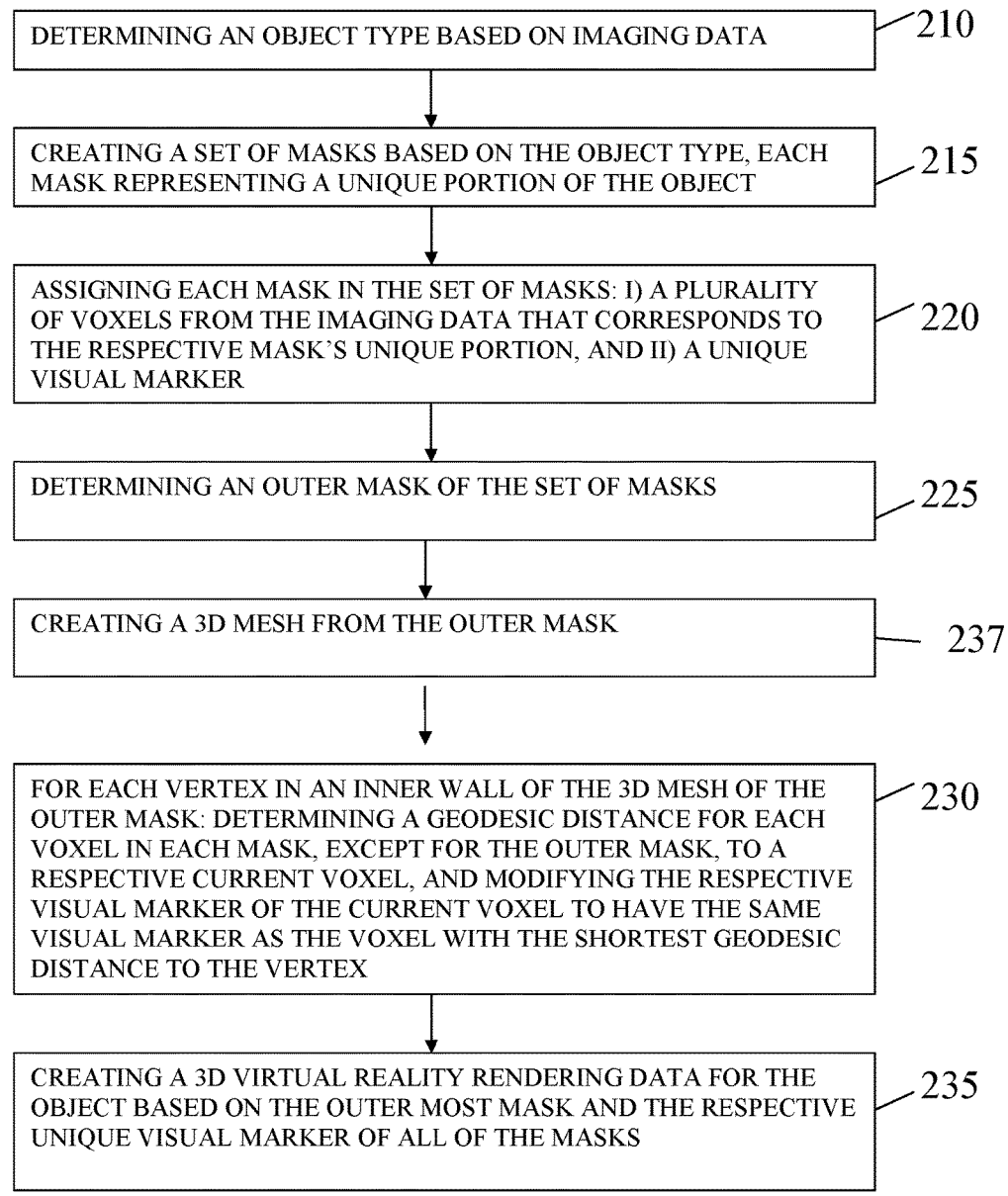
FIG. 2A shows a flowchart of a method according to some embodiments of the present invention.

Reference is made to FIG. 2A, a flowchart of a method for creating a 3D virtual reality or augmented reality rendering of an object from imaging data, according to some embodiments of the present invention. As shown by step 210, an object type may be determined based on imaging data. If the imaging data 131 is of a heart, the object type is determined to be a heart. If the imaging data includes multiple elements (e.g., two heart chambers and corresponding veins) then it can be determined that the elements in the imaging data belong to a heart.

As shown by step 215, a set of masks may be created based on the object type where each mask represents a unique portion of the object. In some embodiments, if the object type is a heart then masks of soft tissue, chambers, Aorta segment, Pulmonary Artery segment may be created, if the object is a head then skull masks, brain masks and/or sinus bone masks may be created. In other cases, e.g., if an electrical device such as a cellphone is the object then case mask, screen mask or masks of electrical circuitry may be created and used as described herein.

In some embodiments, a user may select an outer mask of the object and, in these embodiments, only masks that are inside the selected outer mask. For example, assuming there are masks of for the entire lungs anatomy and the entire heart anatomy (cardiac soft tissue, chambers, Aorta segment, Pulmonary Artery segment), when the user chooses the soft tissue mask, a resulting image may include only the soft tissue, chambers, Aorta and Pulmonary Artery (since they are inside the muscle).

For example, if the object type is a human heart, then a set of masks that correspond to a human heart may be masks of chambers and other portions, as shown, for example, in Table 1 as follows:

TABLE 1

LVMask—Left ventricle mask
RVMask—Right ventricle mask
RAMask—Right atrium mask
LAMask—Left atrium mask
AortaMask—Aorta mask
PAMask—Pulmonary Artery mask
BloodMask—Blood Volume Mask
STMask—Soft tissue Mask In various embodiments, the set of masks for each object type that is input by a user, is generated via another computer program or any combination thereof. As is apparent to one of ordinary skill in the art, the object type can be any object which can be 3D imaged. For example, in addition to medical applications, 3D imaging can be performed in an industrial setting. Industrial 3D imaging data can be of engines, electrical circuits and the like.

As shown by step 220, each of the masks may be assigned a set or plurality of voxels (e.g., some or all of the voxels in imaging data 131). For example, voxels describing, belonging or included in an aorta in imaging data 131 may be assigned to the aorta mask. Each mask may be assigned a visual marker, e.g., a visual marker may be a color. The visual marker can be assigned by a user (e.g., via a user interface), determined by the system based on a type of the mask, or any combination thereof.

As shown by step 225, the outer mask may be identified and/or determined. In some embodiments, the outer mask is received. For example, the outer mask can be defined by a user input. In some embodiments, the outer mask can be determined based on the object type.

Continuing with the above example, where the object type is a heart, soft tissues around the heart may be used for generating the outer mask.

In some embodiments, one or more of the masks is smoothed. In some embodiments, the outer mask is smoothed. For example, if the outer mask is soft tissue of the heart, then because imaging data of the soft tissue of the heart can include noise, the outer mask can be smoothed as known in the art, e.g., to eliminate the noise, and/or unwanted data points. In some embodiments, the outer mask may be smoothing using a box mean filter (for example, one of dimension [3,3, 3]) and using a threshold of 0.5.

In some embodiments, when creating a mesh from a thick mask (e.g., a mask with a width of more than one voxel), the resulting mesh may have inner and outer walls. In these embodiments, the when the outer mask is identified, it can correspond to the outer wall. In these embodiments, voxels that belong to the outer mask, but that are not identified as belonging to the outer mask (e.g., voxels of the inner walls) can be determined.

Figure 2B:
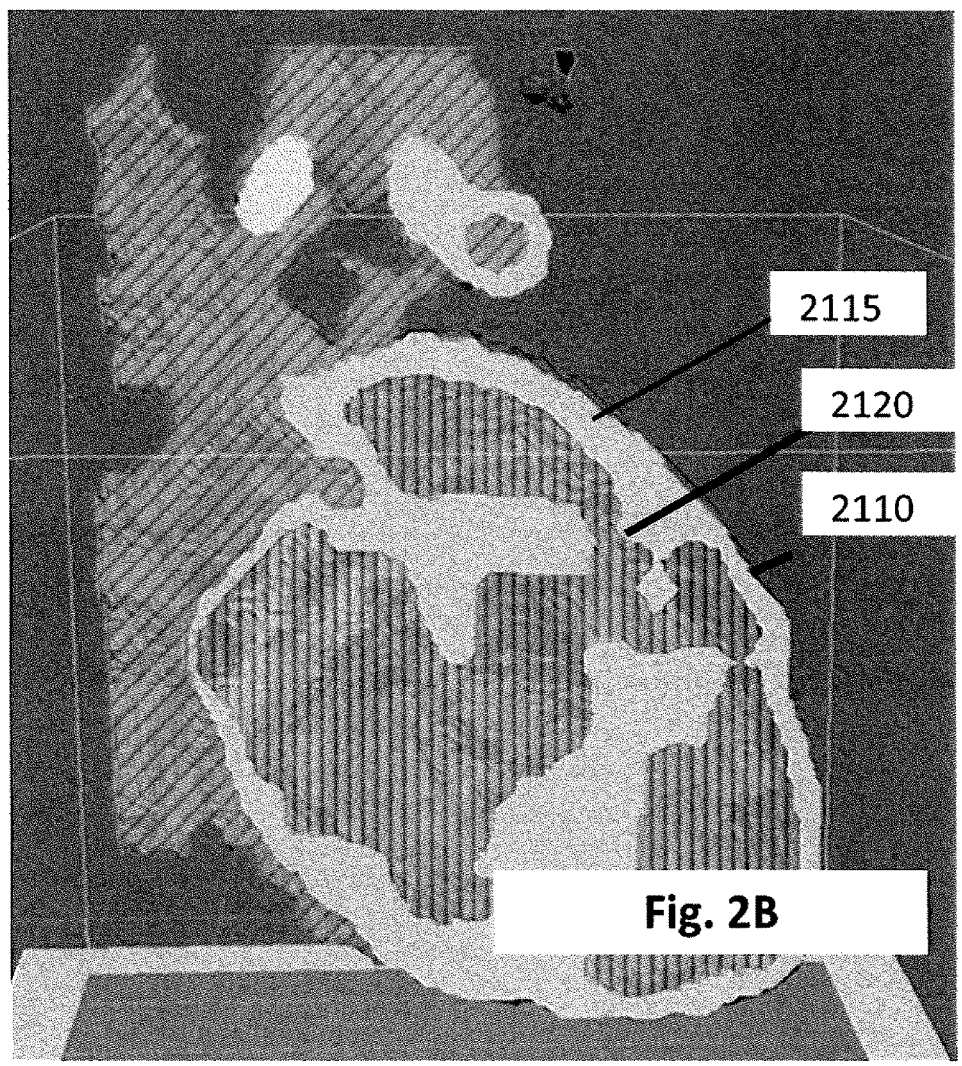
FIG. 2B, shows an example of a cross section of a cardiac mesh having inner and outer walls, according to an illustrative embodiment of the invention.

For example, FIG. 2B, shows an example of a cross section of a heart mesh, with an outer mask having inner and outer walls, according to an illustrative embodiment of the invention. As shown in FIG. 2B, muscle tissue 2115 has a thickness such that its inner walls are indicated by vertical lines and its outer walls are patterned in diagonal lines. Since the 3D mesh may be created from, or based on, the outer mask (e.g., in case of cardiac modeling, the muscle tissue is the outer mask), its inner walls' voxels can be colored by using the colors of the inner masks. Since each voxel can correspond to a specific mask, and each vertex can correspond to a specific mesh, it can follow that a color for each vertex in the inner wall of the mesh can be determined. Since the vertices of the outer mask's mesh may not necessarily be placed on the inner masks voxels (e.g., due to the mesh creation process), a geodesic distance step can be done.

Turning back to FIG. 2A, the method can also involve creating a mesh from the outer mask (Step 237). The method can also involve determining the vertices' color based on a geodesic distance. For each mask in the set of masks except the outer mask: a geodesic distance between each voxel in a respective mask and a vertex in the inner walls of the outer mask mesh may be determined, as shown by step 230.

Continuing with the heart example as described above, determining the geodic distance between each voxel in a respective mask and a vertex in the inner wall of the outer mask's mesh can involve generating a TraverseMask (e.g., which can cover the area of the inner wall of the mesh) by dilating the BloodMask by 1, e.g., as shown in EQN. 1 below:

$$\text{TraverseMask} = \text{BloodMask} \oplus 1 \qquad \text{EQN. 1}$$

Each of the chamber and/or vessel masks (e.g., the LVMask, RVMask) dilating by a 1 voxel radius (e.g., using the "A⊕R" operation as described above).

The geodic distance between each mask and each vertex can be determined. Continuing with the heart example, the geodic distance upon the traverse mask between each vertex and each chamber and vessel masks can be determined. Each vertex can have its visual marker modified to the visual marker of a voxel having the shortest geodesic distance (e.g., is the closest) to the vertex.

In some embodiments, the color of specific masks may be modified via user input. For example, based on user input that indicates that muscles are of interest, voxels that represent muscle tissues (e.g., in a MuscleMask) may be assigned a color selected for muscles (e.g., the color selected for the MuscleMask). Any object or structure may be used to record or represent the mapping of each voxel to a color (e.g., a list, a set of pointers or references and the like).

A colored set of voxels (e.g., as represented by maps) may be produced and used in order to create a 3D virtual reality or augmented reality rendering data for the object. For example, the outermost mask may be augmented by portions of other masks as described (e.g., by associating voxels with the mask and/or coloring voxels as described) such that the mask accurately represents and/or enables creating a view as required by a physician or other user. As shown by step 235, data for 3D virtual reality or augmented reality rendering of the object may be produced based on the outer mask and the respective unique marker of all of the masks. For example, a colored 3D virtual rendering of a heart may be created based on the heart masks as describe in the examples above, e.g., using the known in the art marching cubes algorithm.

In the description and claims of the present application, each of the verbs, "comprise" "include" and "have", and conjugates thereof, are used to indicate that the object or objects of the verb are not necessarily a complete listing of components, elements or parts of the subject or subjects of the verb. Unless otherwise stated, adjectives such as "substantially" and "about" modifying a condition or relationship characteristic of a feature or features of an embodiment of the disclosure, are understood to mean that the condition or characteristic is defined to within tolerances that are acceptable for operation of an embodiment as described. In addition, the word "or" is considered to be the inclusive "or"

rather than the exclusive or, and indicates at least one of, or any combination of items it conjoins.

Descriptions of embodiments of the invention in the present application are provided by way of example and are not intended to limit the scope of the invention. The described embodiments comprise different features, not all of which are required in all embodiments. Some embodiments utilize only some of the features or possible combinations of the features. Variations of embodiments of the invention that are described, and embodiments comprising different combinations of features noted in the described embodiments, will occur to a person having ordinary skill in the art. The scope of the invention is limited only by the claims.

Unless explicitly stated, the method embodiments described herein are not constrained to a particular order in time or chronological sequence. Additionally, some of the described method elements may be skipped, or they may be repeated, during a sequence of operations of a method.

While certain features of the invention have been illustrated and described herein, many modifications, substitutions, changes, and equivalents may occur to those skilled in the art. It is, therefore, to be understood that the appended claims are intended to cover all such modifications and changes as fall within the true spirit of the invention.

Various embodiments have been presented. Each of these embodiments may of course include features from other embodiments presented, and embodiments not specifically described may include various features described herein.

The invention claimed is:

1. A method for creating a three-dimensional (3D) virtual reality or augmented reality rendering of an object from a 3D object, the method comprising:
   receiving a plurality of masks each mask assigned a plurality of voxels, the plurality of masks including an outer mask and a plurality of other masks, and each mask including a unique visual marker and representing a unique portion of the 3D object;
   creating a 3D mesh from the outer mask;
   for each vertex in an inner wall of the 3D mesh of the outer mask:
      a) determining a geodesic distance for each voxel in each mask, except for the outer mask, to a respective current voxel, and
      b) modifying the respective visual marker of the current vertex to have the same visual marker as the voxel with the shortest geodesic distance to the vertex; and
   creating the 3D virtual reality or augmented reality rendering of the object based on the outer mask and the respective unique visual marker of all of the masks.

2. The method of claim 1 wherein the set of masks is based on: determining an object type based on the 3D object;
   creating a set of masks based on the object type;
   assigning each mask in the set of masks i) a plurality of voxels from the 3D object that corresponds to the respective mask's unique portion and ii) the unique visual marker; and
   determining an outer mask of the set of masks.

3. The method of claim 1 further comprising for each voxel in the plurality of voxels that is not assigned to a mask:
   a) determining one mask from the set of masks having a voxel that is within a nearest distance to the current voxel, and
   b) assigning a visual marker to the current voxel that is the same as the unique visual marker of the one mask.

4. The method of claim 1 further comprising modifying the outer mask by applying a box filter that has a predetermined threshold.

5. The method of claim 1 wherein determining the outer mask is based on user input, the object type, or any combination thereof.

6. The method of claim 1 wherein the unique visual marker is a color marker, a pattern, or any combination thereof.

7. The method of claim 1 further comprising displaying by a virtual reality or augmented reality device or an augmented reality device the 3D virtual reality or augmented reality rendering.

8. A non-transient computer readable medium containing program instructions for causing a computer to perform the method of:
   receiving a plurality of masks each mask assigned a plurality of voxels, the plurality of masks including an outer mask and a plurality of other masks, and each mask including a unique visual marker and representing a unique portion of the 3D object;
   creating a 3D mesh from the outer mask;
   for each vertex in an inner wall of the 3D mesh of the outer mask:
      c) determining a geodesic distance for each voxel in each mask, except for the outer mask, to a respective current voxel, and
      d) modifying the respective visual marker of the current vertex to have the same visual marker as the voxel with the shortest geodesic distance to the vertex; and
   creating the 3D virtual reality or augmented reality rendering of the object based on the outer mask and the respective unique visual marker of all of the masks.

9. The non-transient computer readable medium of claim 8 wherein the set of masks is based on:
   determining an object type based on the 3D object;
   creating a set of masks based on the object type;
   assigning each mask in the set of masks i) a plurality of voxels from the 3D object that corresponds to the respective mask's unique portion and ii) the unique visual marker; and
   determining an outer mask of the set of masks.

10. The non-transient computer readable medium of claim 8 wherein for each voxel in the plurality of voxels that is not assigned to a mask:
    c) determining one mask from the set of masks having a voxel that is within a nearest distance to the current voxel, and
    d) assigning a visual marker to the current voxel that is the same as the unique visual marker of the one mask.

11. The non-transient computer readable medium of claim 8 further comprising modifying the outer mask by applying a box filter that has a predetermined threshold.

12. The non-transient computer readable medium of claim 8 wherein determining the outer mask is based on user input, the object type, or any combination thereof.

13. The non-transient, computer readable medium of claim 8 wherein the unique visual marker is a color marker, a pattern, or any combination thereof.

14. The non-transient computer readable medium of claim 8 further comprising displaying by a virtual reality or augmented reality device or an augmented reality device the 3D virtual reality or augmented reality rendering.

* * * * *